US010280446B2

(12) United States Patent
Mach et al.

(10) Patent No.: US 10,280,446 B2
(45) Date of Patent: May 7, 2019

(54) METHODS AND ARTICLES FOR DETECTING DEOXYRIBONUCLEASE ACTIVITY

(71) Applicant: 3M INNOVATIVE PROPERTIES COMPANY, Saint Paul, MN (US)

(72) Inventors: Patrick A. Mach, Shorewood, MN (US); Michelle L. Rosauer, North St. Paul, MN (US); Michael E. Hughes, Burnsville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 116 days.

(21) Appl. No.: 15/651,164

(22) Filed: Jul. 17, 2017

(65) Prior Publication Data
US 2017/0314059 A1 Nov. 2, 2017

Related U.S. Application Data

(62) Division of application No. 14/529,481, filed on Oct. 31, 2014, now Pat. No. 9,738,919, which is a division of application No. 13/203,015, filed as application No. PCT/US2010/024932 on Feb. 22, 2010, now Pat. No. 8,889,351.

(60) Provisional application No. 61/155,666, filed on Feb. 26, 2009.

(51) Int. Cl.
*C12Q 1/00* (2006.01)
*C12Q 1/04* (2006.01)
*C12Q 1/34* (2006.01)

(52) U.S. Cl.
CPC ............... *C12Q 1/34* (2013.01); *C12Q 1/04* (2013.01); *G01N 2333/31* (2013.01); *G01N 2333/922* (2013.01)

(58) Field of Classification Search
CPC ...... C12Q 1/04; C12Q 1/34; G01N 2333/922; G01N 2333/31
See application file for complete search history.

(56) References Cited

U.S. PATENT DOCUMENTS

| 4,241,181 A | 12/1980 | Lund ................................ 435/34 |
| 4,565,783 A | 1/1986 | Hansen et al. ................. 435/299 |
| 5,089,413 A | 2/1992 | Nelson et al. ................. 435/254 |
| 5,137,812 A | 8/1992 | Matner ........................... 435/38 |
| 5,232,838 A | 8/1993 | Nelson et al. .................. 435/30 |
| 5,443,963 A | 8/1995 | Lund ................................ 435/34 |
| 5,448,652 A | 9/1995 | Vaidyanathan et al. ...... 382/165 |
| RE35,286 E | 6/1996 | Nelson et al. ................. 435/243 |
| 5,618,729 A | 4/1997 | Izraelevitz et al. ........... 435/288 |
| 5,681,712 A | 10/1997 | Nelson ............................ 435/30 |
| 5,879,635 A | 3/1999 | Nason ............................ 422/102 |
| 6,022,682 A | 2/2000 | Mach et al. ...................... 435/4 |
| 6,107,054 A | 8/2000 | Gibbs ............................. 435/32 |
| 6,153,400 A | 11/2000 | Matsumura et al. ........... 435/32 |
| 6,243,486 B1 | 6/2001 | Weiss ............................ 382/133 |
| 7,087,401 B2 | 8/2006 | Sandberg et al. .............. 435/34 |
| 8,889,351 B2 | 11/2014 | Mach ....................... C12Q 1/04 435/34 |
| 2003/0186350 A1 | 10/2003 | Newell .......................... 435/32 |
| 2004/0101954 A1 | 5/2004 | Graessle et al. .............. 435/288 |
| 2004/0102903 A1 | 5/2004 | Graessle et al. ................ 702/19 |
| 2008/0309914 A1 | 12/2008 | Cantin et al. .................... 356/4 |

FOREIGN PATENT DOCUMENTS

| EP | 0 956 362 | 11/1999 | ............... C12Q 1/14 |
| GB | 2 020 017 | 11/1979 | ............ G01N 31/14 |
| WO | WO 1998/06870 | 2/1998 | ............... C12Q 1/14 |
| WO | WO 2005/024047 | 3/2005 | ............... C12Q 1/00 |

OTHER PUBLICATIONS

Ball, T.K. et al.; "The extracellular nuclease gene of *Serratia marcescens* and its secretion from *Escherichia coli*"; Gene, Elsevier; vol. 57; 1987; pp. 183-192.
Blackburn, C. et al.; "Evaluation of Pretrifilm™ methods for enumeration of aerobic flora and coliforms in a wide range of foods"; Letters in Applied Microbiology; vol. 22; 1996; pp. 137-140.
Chaudhuri, P. et al.; "Modified methods for simple and rapid detection of bacterial deoxyribonuclease production"; Journal of Microbiological Methods; vol. 16; 1992; pp. 307-311.
Elder, et al.; "Rapid deoxyribonuclease test with methyl green"; Journal of Clinical Microbiology; vol. 6, No. 3; 1977; pp. 312-313.
James, G.A. et al.; "Digital Image Analysis of Growth and Starvation Responses of a Surface-Colonizing *Acinetobacter* sp."; Journal of Bacteriology; vol. 177, No. 4; pp. 907-915.
Kurnick, N.B. et al.; "Acid Desoxyribonuclease Assay by the Methyl Green Method"; Biochem. Biophys. Acta.; vol. 39; 1960; pp. 226-231.
Lachica, R.V.F. et al.; "Metachromatic Agar-Diffusion Methods for Detecting Staphylococcal Nuclease Activity"; Applied Microbiology vol. 21, No. 4; 1971; pp. 585-587.
Langlois, B.E. et al.; "Comparison of Methods for Determining DNase and Phosphatase Activities of Staphylococci"; Journal of Clinical Microbiology; vol. 27, No. 5; 1989; pp. 1127-1129.
Porter, A.C.; "Use of Methyl Green-DNA Agarose for Detecting Deoxyribonuclease Activity in Polyacrylamide Gels"; Analytical Biochemistry; vol. 117; 1981; pp. 28-31.
Sinicropi, D. et al.; "Colorimetric Determination of Dnase I Activity with a DNA-Methyl Green Substrate"; Analytical Biochemistry; vol. 222; 1994; pp. 351-358.

(Continued)

Primary Examiner — Satyendra K Singh
(74) Attorney, Agent, or Firm — Eric E. Silverman

(57) ABSTRACT

The disclosure provides articles and methods useful for detecting a discrete source of DNase activity. DNase-producing microorganisms can be detected. The device can further include selective agents and/or indicators to differentiate groups or species microorganisms. Methods of use include detecting or enumerating DNase-producing microorganisms.

4 Claims, 5 Drawing Sheets

(56) References Cited

OTHER PUBLICATIONS

Smith, P.B. et al.; "Improved Medium for Detecting Deoxyribonuclease-Producing Bacteria"; Applied Mirobiology; vol. 18, No. 6; 1969; pp. 991-993.

Tolun, G. et al.; "A real-time Dnase assay (ReDA) based on PicoGreen® fluorescence" Nucleic Acids Research; vol. 31, No. 18 e111, 2003; (6 pgs.).

Waller, J.R. et al.; "An evaluation of five techniques used to detect deoxyribonuclease production by bacteria"; Journal of Microbiological Methods; vol. 3; 1985; pp. 303-309.

Waller, J.R. et al.; "Improvement of Two Toluidine Blue O-Mediated Techniques for Dnase Detection"; Journal of Clinical Microbiology; vol. 21, No. 2; 1985; pp. 195-199.

Zimbro, M.J. et al.; "Difco™ & BBL™ Manual—Manual of Microbiological Culture Media"; Second Edition; BD Diagnostics—Diagnostic Systems, Spark, MD 21152; 2009; pp. 175-178.

METHODS AND ARTICLES FOR DETECTING DEOXYRIBONUCLEASE ACTIVITY

CROSS REFERENCE TO RELATED APPLICATIONS

This application is a division of U.S. Ser. No. 14/529,481, filed Oct. 31, 2014, which is a division of U.S. Ser. No. 13/203,015, filed Oct. 17, 2011 (now U.S. Pat. No. 8,889, 351), which is a national stage filing under 35 U.S.C. 371 of PCT/US2010/024932, filed Feb. 22, 2010, claims priority to U.S. Provisional Patent Application No. 61/155,666, filed Feb. 26, 2009, which are incorporated herein by reference in their entirety.

BACKGROUND

DNA nucleases (DNases) are ubiquitous in biological cells and are involved in a number of cellular functions including, for example, DNA replication and repair. Certain microorganisms (e.g., *Branhamella catarrhalis, Staphylococcus aureus, Serratia marcescens, Streptococcus pyogenes, Bacillus subtilis, Vibrio alginolyticus, Cryptococcus neoformans, Fusarium solani*) produce DNases that are excreted out of the cells.

DNA nucleases (DNases) are used in a variety of research and diagnostic applications. DNase activity assays have been developed to monitor the enzyme. In research applications, DNase assays frequently employ radiolabeled DNA substrates and require separation of the products of the reaction from the unreacted substrate before quantification of enzyme activity. Tolun and Myers developed a continuous DNase assay based on the differential fluorescence output of a DNA dye ligand (Nuc. Acid Res. 31:e111, 2003). Their assay requires a spectrofluorometer to detect the DNase activity.

DNA nucleases have been used to detect microorganisms, such as *Staphylococcus aureus*, which excrete the enzyme into the environment surrounding the cells or colonies of cells. Culture media comprising nutrients, agar, and an indicator system comprising DNA (typically, high molecular weight DNA or large oligonucleotides) and either 100 µg/mL toluidine blue 0 or 50 µg/mL methyl green have been used in methods to detect *S. aureus*. The culture methods typically require laborious procedures to prepare the agar which, once prepared, must be used within a relatively short period of time.

There exists a need for stable articles and simple, inexpensive methods to detect DNase activity and to detect microorganisms that produce DNase enzymes.

SUMMARY

In view of the current general methods to detect DNase activity, which require sophisticated techniques and/or expensive equipment, the present disclosure includes simple methods that can be performed with a low-cost imaging system. In some embodiments, the inventive methods provide for quantitative or semi-quantitative determinations of DNase activity. In some embodiments, the inventive methods provide for quantitative or semi-quantitative determinations of microorganisms.

Additionally, the present disclosure includes simple, inexpensive articles and methods to detect DNase-producing microorganisms. The inventors have observed that, at concentrations of methyl green that are typically used in the art, the growth of some DNase-producing microorganisms can be significantly inhibited. They have discovered a method that uses surprisingly low concentrations of methyl green to detect DNase-producing microorganisms. The lower concentrations of dye permit better growth and/or recovery from environmental or metabolic stresses and, thus, faster detection of DNase-producing microorganisms. Additionally, by using an imaging system and by biasing the wavelengths of light used to collect, analyze, and/or display an image, the inventive methods provide for a simpler, earlier, and more consistent determination of DNase activity.

Thus, in one aspect, the present disclosure provides a method of detecting a microorganism. The method can comprise providing a dry composition and a sample suspected of containing a microorganism. The dry composition can comprise a cold water-soluble gelling agent and a DNase indicator system including methyl green and DNA. The method can further comprise contacting a predetermined volume of aqueous liquid comprising the sample with the dry composition to form a hydrogel, incubating the rehydrated hydrogel for a period of time, and detecting a microorganism.

In some embodiments, the dry composition can further comprise a nutrient, a selective agent, or an indicator. In some embodiments, the method can further comprise the step of providing a nutrient, a selective agent, an indicator, or any combination of two or more of the foregoing; wherein the aqueous liquid comprising the sample further comprises the nutrient, the selective agent, the indicator, or any combination of two or more of the foregoing. In some embodiments, the selective agent can comprise an antibiotic. In some embodiments, the antibiotic is selected from the group consisting of a cephalothin, cefazolin, cephradine, cephalexin, cefadroxil, cefamandole, cefoxitin, cefaclor, cefuroxime, cefuroxime axetil, loracarbef, cefonicid cefotetan, ceforanide, cefotaxime, cefpodoxime proxetil, ceftizoxime, cefixmeceftriaxone, cefoperazone, ceftazidime, moxlactam, cefipime, cefpirome, and oxacillin.

In some embodiments, the method can further comprise providing an imaging system and obtaining an image of the hydrogel with the imaging system. In these embodiments, detecting a microorganism can comprise displaying (e.g., on a computer monitor), printing, or analyzing the image of the hydrogel.

In some embodiments, the method can further comprise enumerating one or more types of microorganisms.

In another aspect, the present disclosure provides a method of detecting deoxyribonuclease activity. The method can comprise providing a hydrogel comprising a DNase indicator system including methyl green and DNA, and a sample suspected of containing a discrete source of deoxyribonuclease activity. The methyl green can be from at least about 5 µg/mL to no more than 49 µg/mL in the hydrogel. The method further can comprise contacting, for a predetermined period of time, the sample and the hydrogel, and detecting deoxyribonuclease activity.

In another aspect, the present disclosure provides a method of detecting deoxyribonuclease activity. The method can comprise providing a hydrogel comprising a DNase indicator system including methyl green and DNA, a sample suspected of containing a discrete source of deoxyribonuclease activity, and an imaging system. The method further can comprise contacting, for a predetermined period of time, the sample and the hydrogel. The method further can comprise obtaining an image of the hydrogel with the imaging system and detecting a discrete source of deoxyribonuclease activity, wherein detecting deoxyribonuclease activity comprises displaying, printing, or analyzing the image of the hydrogel.

In any of the above embodiments, the hydrogel can further comprise a nutrient, a selective agent, an antibiotic, and/or an indicator. In any of the above embodiments, the method can further comprise the step of providing a nutrient, a selective agent, an indicator, or any combination of two or more of the foregoing; wherein contacting for a predetermined period of time comprises contacting the sample and the hydrogel with the nutrient, the selective agent, the indicator, or any combination of two or more of the foregoing. In any of the above embodiments, the selective agent can comprise an antibiotic. In any of the above embodiments, the antibiotic is selected from the group consisting of a cephalothin, cefazolin, cephradine, cephalexin, cefadroxil, cefamandole, cefoxitin, cefaclor, cefuroxime, cefuroxime axetil, loracarbef, cefonicid cefotetan, ceforanide, cefotaxime, cefpodoxime proxetil, ceftizoxime, cefixmeceftriaxone, cefoperazone, ceftazidime, moxlactam, cefipime, cefpirome, and oxacillin.

In any of the above embodiments including an imaging system, the imaging system can comprise an illumination source and the step of obtaining an image of the hydrogel can comprise illuminating the hydrogel. In any of the above embodiments including an imaging system, illuminating the hydrogel can comprise illuminating the hydrogel with a limited band of visible wavelengths. In any of the above embodiments including an imaging system, the hydrogel can be illuminated with visible wavelengths selected from wavelengths in the range of about 625 nm to about 740 nm. In any of the above embodiments including an imaging system, obtaining an image of the article can comprise using a bias filter to illuminate the hydrogel or to collect the image. In any of the above embodiments including an imaging system, analyzing the image can comprise analyzing selected wavelengths of the image.

In another aspect, the present disclosure provides a detection article. The detection article can comprise a body member that includes a self-supporting, waterproof substrate having upper and lower surfaces. A dry coating comprising a cold water-soluble gelling agent and a DNase indicator system can be adhered uniformly onto a portion of at least one surface of the body member. The DNase indicator system can comprise DNA and methyl green. In some embodiments, after contact with a predetermined volume of liquid, the gelling agent can forms a hydrogel with the concentration of methyl green in the hydrogel at least about 5 μg/mL to about 100 μg/mL.

In some embodiments, the coating further can comprise a nutrient medium, an indicator, a selective agent, or a combination of any two or more of the foregoing. In some embodiments, the selective agent can select for the growth of *Staphylococcus aureus*. In some embodiments, the selective agent can comprise an antibiotic. In some embodiments, the antibiotic is selected from the group consisting of a cephalothin, cefazolin, cephradine, cephalexin, cefadroxil, cefamandole, cefoxitin, cefaclor, cefuroxime, cefuroxime axetil, loracarbef, cefonicid cefotetan, ceforanide, cefotaxime, cefpodoxime proxetil, ceftizoxime, cefixmeceftriaxone, cefoperazone, ceftazidime, moxlactam, cefipime, cefpirome, and oxacillin.

In another aspect, the present disclosure provides a kit. The kit can comprise a detection article comprising a dry coating including a cold water-soluble gelling agent, DNA, and methyl green. In some embodiments, the detection article can further comprise a nutrient, a selective agent, an indicator, or a combination of any two or more of the foregoing. In some embodiments, the kit can further comprise an antibiotic.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a sample suspected of containing "a" microorganism can be interpreted to mean that the liquid can include "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

FIG. 7b is a graph of the pixel intensity data for the pixels located on line A of FIG. 7a.

FIG. 8b is a graph of the pixel intensity data for the pixels located on line A of FIG. 8a.

DETAILED DESCRIPTION

Figure 1:
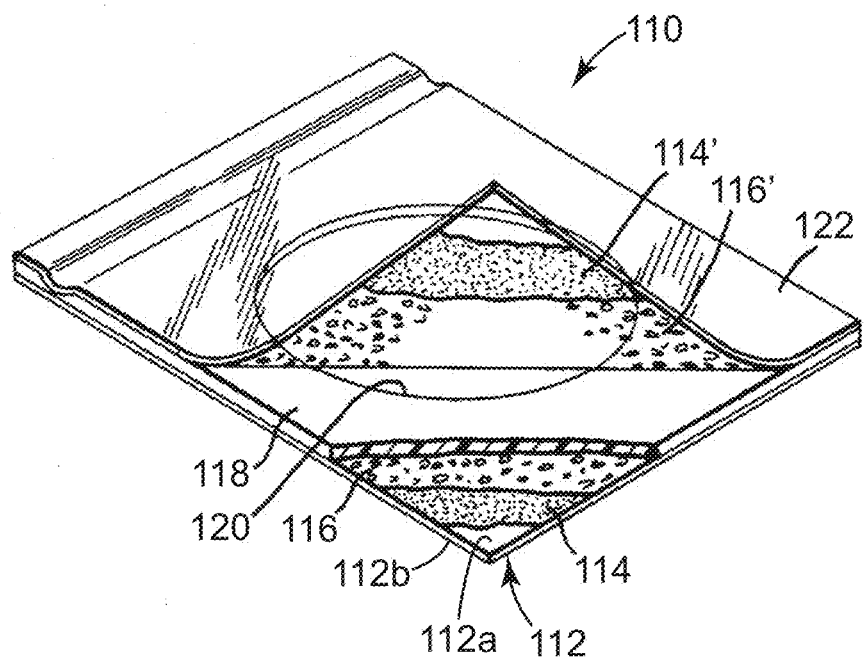
FIG. 1 is a top perspective view, partially in section, of an embodiment of a thin film culture device comprising a spacer.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting and differentiating microorganisms in a sample. In particular, the disclosure relates to the detection and differentiation of DNase-producing microorganisms. In some embodiments, the methods and articles disclosed herein can be used to detect microorganisms that produce a heat-stable DNase known as thermonuclease (TNase). In some embodiments, detection of DNase-producing microorganisms comprises enumerating the DNase-producing microorganisms in the sample. Suitable samples can be obtained or derived from a variety of sources.

The term "source" is generally used to refer to the food or nonfood desired to be tested for microorganisms. The source can be a solid, a liquid, a semi-solid, a gelatinous material, and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a culture plate device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, nonpotable water, wood, soil, sediment, medicines, cosmetics, dietary supplements (e.g., ginseng capsules), pharmaceuticals, fomites, other suitable non-comestible materials, and combinations thereof.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, tongue depressors, filters, pipettes, pipette tips, and siphon hoses.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "microorganism" is generally used to refer to any prokaryotic or eukaryotic microscopic organism capable of growing and reproducing in culture medium, including without limitation, one or more of bacteria (e.g., motile or vegetative, Gram positive or Gram negative), bacterial spores or endospores, fungi (e.g., yeast, filamentous fungi, fungal spores). In some cases, the microorganisms of particular interest are those that are pathogenic, and the term "pathogen" is used to refer to any pathogenic microorganism. Examples of pathogens can include, but are not limited to, members of the family *Enterobacteriaceae*, or members of the family *Micrococcaceae*, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacteria* spp. Particular examples of pathogens can include, but are not limited to, *Escherichia coli* including enterohemorrhagic *E. coli* e.g., serotype O157:H7, *Pseudomonas aeruginosa, Bacillus cereus, Bacillus anthracis, Branhamella catarrhalis, Salmonella enteritidis, Salmonella typhimurium, Listeria monocytogenes, Clostridium botulinum, Clostridium perfringens, Staphylococcus aureus*, methicillin-resistant *Staphylococcus aureus, Campylobacter jejuni, Yersinia enterocolitica, Vibrio vulnificus, Clostridium difficile*, vancomycin-resistant *Enterococcus, Streptococcus pyogenes, Serratia marcescens*, and *Enterobacter sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

DNase Indicator System

Articles and methods of the present disclosure include a DNase indicator system. The DNase indicator system comprises DNA and methyl green. Optionally, the indicator system can further comprise a binder such as λ-carrageenan and/or a buffer. In use, the DNase indicator system is mixed with a gelling agent, such as agar or a cold-water soluble gelling agent (e.g., guar gum, xanthan gum, locust bean gum, and combinations thereof). In some embodiments, the DNase indicator system mixed with a gelling agent is coated on a substrate, as described herein.

Methyl green forms a stable complex with DNA molecules. When the methyl green-complexed DNA is depolymerized (e.g., by enzymatic hydrolysis), the methyl green becomes colorless. Smith et al. (1969, Appl. Microbiol. 18:991) demonstrated that DNase-producing bacteria could be detected in microbiological media containing DNA and methyl green.

The DNA in the indicator system typically is readily available commercially (for example, salmon sperm DNA available from Sigma-Aldrich, St. Louis, Mo.), and may be any DNA of sufficient molecular weight such that it is capable of forming a green-colored complex with methyl green. A salt form of methyl green (e.g., methyl green zinc chloride salt) can be used in the indicator system and can be obtained from, for example Sigma-Aldrich (St. Louis, Mo.).

Culture Devices:

The present disclosure includes articles for the detection of DNase activity. The detection articles include culture devices for growing and detecting microorganisms. Culture devices of the present invention include, for example, thin film culture plate devices. Thin film culture plate devices are typically more compact than traditional agar petri dishes and typically contain dry, rehydratable culture medium to support the growth of certain microorganisms. Non-limiting examples of thin film culture plate devices include the coated-substrate devices disclosed in U.S. Pat. Nos. 4,565,783; 5,089,413; and 5,681,712; each of which is incorporated herein by reference in its entirety.

Figure 2:
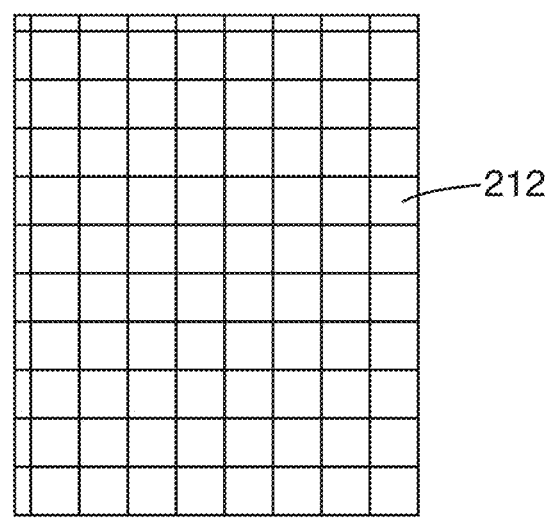
FIG. 2 is a top view of one embodiment of a self-supporting substrate comprising a grid pattern.

FIG. 1 illustrates an embodiment of a thin film culture device in accordance with the present invention. The culture device 110 includes a body member comprising a self-supporting water-proof substrate 112 having upper and lower surfaces (112a and 112b, respectively). Substrate 112 can be a relatively stiff film (e.g., polyester, polypropylene or polystyrene), which will not absorb or otherwise be affected by water. The substrate 112 may be either transparent or opaque, depending on whether one wishes to view bacterial colonies through the substrate. To facilitate the counting of bacterial colonies, the substrate 212 can have a grid pattern (e.g., squares) printed thereon, as shown in FIG. 2.

Referring to FIG. 1, substrate 112 can be coated on its upper surface 112a with a layer of an adhesive 114 which serves to hold the dry gelling agent, DNase indicator system, and/or nutrients in a uniform monolayer for easy hydration. Adhesive 114 should be coated onto substrate 112 in a thickness which is preferably less than the diameter of the particles of the powdered gelling agent and/or nutrients. The object is to apply enough adhesive to adhere the particles to the substrate but not so much that the particles become completely embedded in the adhesive. A uniform monolayer of cold-water-soluble powder 116 is desired with sufficient surface area exposed for hydration. Also shown in FIG. 1 are optional adhesive 114' and cold-water-soluble powder 116' layers on cover sheet 122. When hydrated with an aqueous solution (e.g., the sample and/or an aqueous suspending medium, such as water or a buffer), the gelling agent forms a hydrogel.

In some embodiments, adhesive 114 can comprise a water-based adhesive composition. Preferably, the layer of water-based adhesive 114 is sufficiently transparent when wetted by an aqueous test sample to enable the viewing of the colonies of microorganisms. The water-based adhesive composition can incorporate one or more hydrophilic agents, including nutrients, selective agents, indicators (e.g., DNase indicator system, enzyme substrates, dyes), or combinations thereof. The specific nutrients and/or selective agents used in the water-based adhesive composition will be apparent to those skilled in the art in view of the present specification depending upon the particular organisms to be grown and/or to be selectively detected (e.g., dyed) or inhibited.

An exemplary useful class of selective agents include dyes that are metabolized by, or otherwise react with, growing microorganisms, and in so doing cause the microbial colonies to be colored or fluoresce for ease of detection and/or quantitation by a technician or by an automated reader. Nonlimiting examples of such dyes include triphenyltetrazolium chloride, p-tolyltetrazolium red, tetrazolium violet, veratryl tetrazolium blue, neutral red, phenol red, chlorophenol red, and 5-bromo-4-chloro-3-indolyl phosphate disodium salt. However, it will be appreciated that other suitable dyes can be used depending on the particular organism(s) to be identified. It will be appreciated by a person of ordinary skill in the art that any indicator, dye, selective agent, enzyme substrate, or nutrient used in accordance with the present invention should not substantially inhibit DNase activity nor should it substantially interfere with the observation and imaging of the DNase indicator system described herein.

A buffering reagent, such as sodium carbonate, can be employed to provide a medium exhibiting a neutral pH and "Cab-O-Sil M-5" can be employed as a processing aid, as described in U.S. Pat. No. 4,565,783, which is incorporated herein by reference in its entirety. Of course, the particular coating mixture (e.g., nutrients, indicators, and/or gelling agents) used for powder 116 may be adjusted depending upon the type of microorganisms to be grown.

It is contemplated that articles of the present disclosure can include differential indicators. As used herein, "differential indicator" refers to a reagent added to the medium that will indicate the presence of certain microorganisms and not other microorganisms. Nonlimiting examples of differential indicators include dyes (e.g., stains, pH indicators, redox indicators), enzyme substrates (e.g., chromogenic or fluorogenic substrates for phosphatases, glycosidases, peptidases, nucleases, lipases, and the like), and specific nutrients (e.g., fermentable carbohydrates, amino acids) which, when metabolized by certain microorganisms, produce a detectable reaction (e.g., a pH change associated with a colony).

In some embodiments, one or more differential indicators can be added to the thin film culture device in the water-based composition that is coated onto the substrate. In some embodiments, one or more differential indicators can be added to the liquid sample that is added to the culture device. In some embodiments, one or more differential indicators can be added to the culture device, after hydration of the culture device. An example of a method involving the use of a differential indicator added to the culture device after hydration is the method wherein an article for the detection of thermonuclease is added to the culture device after incubation such as described in U.S. Pat. No. 6,022,682 which is incorporated herein by reference in its entirety.

It is also contemplated within the scope of the invention that powder 116 may optionally include reagents necessary for carrying out certain biochemical tests for microorganism identification. Such reagents (e.g. an enzyme substrate), which undergo a color change in the presence of a particular type of microorganism, may be included in the powder 116 or adhesive 114.

In another embodiment of the invention, powder 116 may comprise a coating that includes a mixture of a gelling agent and a nutrient, a selective agent, and/or an indicator which has been dissolved or suspended in a solution, coated and dried onto substrate 112. In this embodiment, the coating is substantially water-free (i.e., the coating has a water content no greater than about the water content of the dehydrated coating once it has been permitted to equilibrate with the ambient environment).

As depicted in FIG. 1, the body member can include a spacer 118 applied to the upper surface of substrate 112, the spacer 118 comprising a circular aperture 120 cut through the center to expose the powder 116 on substrate 112. The walls of aperture 120 provide a well of predetermined size and shape to confine the medium following hydration. Spacer 118 should be thick enough to form a well of the desired volume, e.g., 1, 2 or 3 milliliters. Closed cell polyethylene foam is a preferred material for spacer 118, but any material which is hydrophobic (non-wetting), inert to microorganisms, and capable of withstanding sterilization may be used. In some embodiments (not shown), the spacer 118 can comprise a plurality of apertures 20 (e.g., 2, 3, 4, 5, 6, 7, 8, 9, 10, 12, 15, or 20 apertures), each of which can be inoculated with a distinct liquid sample.

Spacer 118 can include relatively thick designs, such as those described in U.S. Pat. No. 5,681,712, which is incorporated herein by reference in its entirety. One purpose of the thicker apertured spacer 118 is to locate and protect membranes (e.g. microporous filter membranes) placed in the aperture 120 of the spacer 118 (not shown). Another purpose of the thicker spacer 118 is to reduce or prevent contact by cover sheet 122 with the growing colonies of microorganisms (i.e., provide a "head space" between the growth surface and the cover sheet 122, which can also provide increased aeration for growing colonies of microorganisms).

The thickness of spacer 118 should be sufficient to enclose the liquid volume added to the culture device when the device is inoculated. Depending upon the thickness of the membrane, when used, the spacer can be at least about 0.5 mm thick, about 1 mm thick, about 1.5 mm thick and about 2 mm thick.

Figure 3:
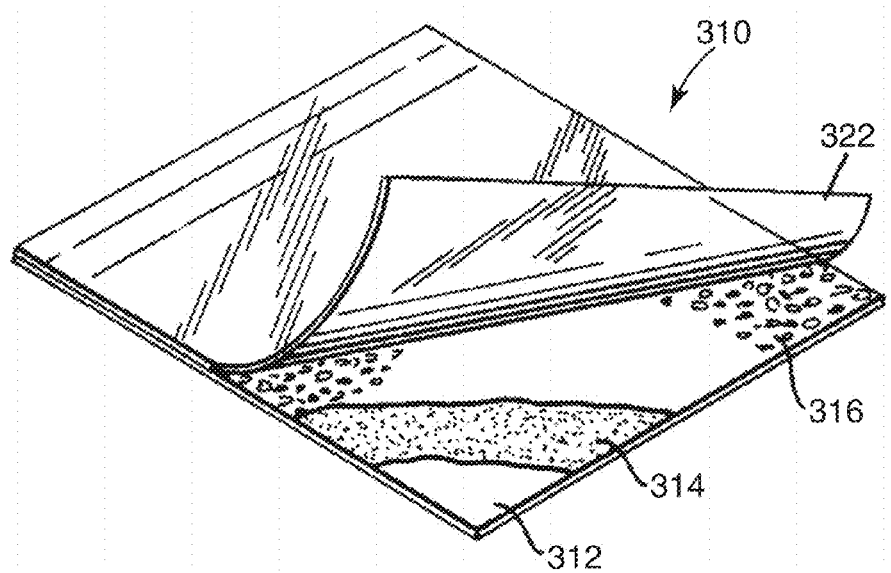
FIG. 3 is a top perspective view, partially in section, of an embodiment of a thin film culture device.

FIG. 3 shows another embodiment of a thin film culture device 310. This embodiment includes substrate 312, adhesive 314, cold-water-soluble powder 316, and cover sheet 322, as described in FIG. 1. The DNase indicator system may be included in the cold-water soluble powder 316. In contrast to the culture device 110 of FIG. 1, the device 310 of FIG. 3 does not include a spacer to confine the sample during inoculation. A template, e.g., a weighted ring (not shown), may be applied temporarily to the outside of cover sheet 322, after closing, to confine the sample to a specific region while the cold-water-soluble powder 316 forms a gel. In some embodiments, the device 310 can be inoculated with a plurality (e.g., 2, 3, 4, 5, 6, 7, 8, 9, 10, 12, 15, or 20) of distinct liquid samples, using appropriate spacing and templates to confine the separate samples to distinct portions of the powder 316 of the culture device 310. When hydrated with an aqueous solution (e.g., the sample and/or an aqueous suspending medium, such as water or a buffer), the cold-water soluble powder comprising a gelling agent forms a hydrogel.

Figure 4:
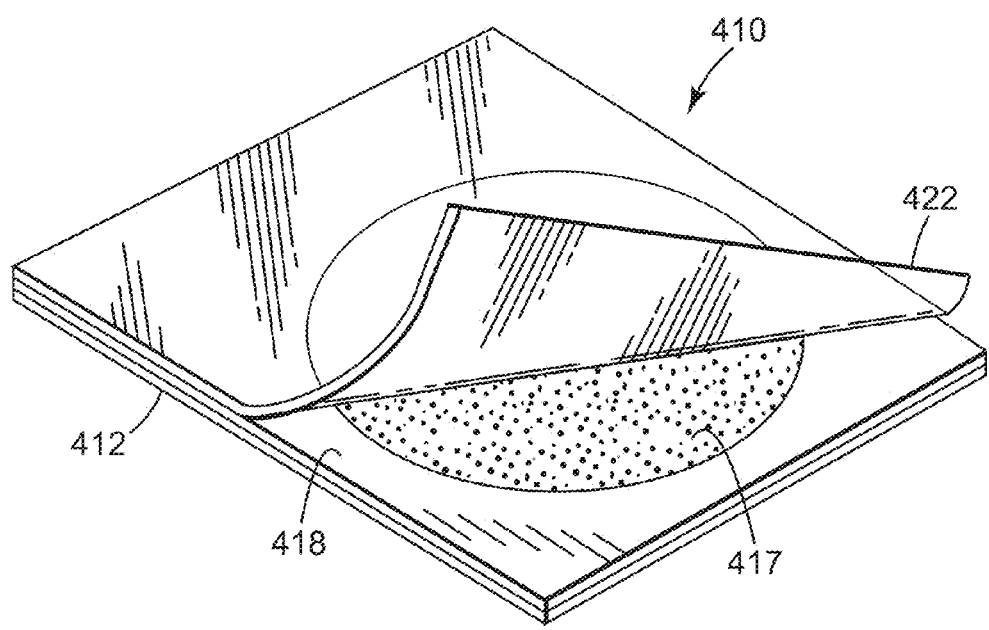
FIG. 4 is a top perspective view, partially in section, of an embodiment of a thin film culture device comprising a spacer.

FIG. 4 illustrates another embodiment of a thin film culture device 410 in accordance with the present invention. Culture device 410 includes body member 411 comprising self-supporting substrate 412 having upper and lower surfaces 412a and 412b, respectively. Substrate 412 is coated on its upper surface 412a with a layer of adhesive 414. Cold-water-soluble powder 416, comprising one or more gelling agents, is adhered in a thin, relatively uniform layer to the adhesive 414. Once inoculated with an aqueous test sample (not shown), the layer of cold-water-soluble powder 416, which may include a DNase indicator system, quickly hydrates to form a reconstituted medium (not shown), which in turn is capable of growing microorganisms present either in a liquid inoculum or on the surface of a membrane such as a test sample microorganism filter (not shown). Spacer 418 partially covers substrate 412 and the surface of powder 416 and contains aperture 420. In addition, thin film culture device 410 optionally includes cover sheet 422, to cover the reconstituted medium formed after addition of the aqueous test sample. FIG. 4 also shows a membrane 426 and microorganism colonies 428 growing thereon. In the illustrated embodiment, membrane 426 is a microporous membrane through which a liquid sample has been filtered in order to trap any bacteria, if present in the sample, thereon. Suitable microporous membranes do not substantially interfere with DNase enzyme activity or with the interaction between DNase enzyme activity and the DNase indicator system. Additionally, suitable microporous membranes are substantially transparent when contacted with a hydrogel.

It is possible to use air-permeable membrane layers in the devices of the present invention as described in U.S. Pat. No. 5,232,838, provided the air-permeable membrane does not substantially interfere with DNase activity or the observation and imaging of DNase activity. The air permeable layer can be "sandwiched" between the substrate and the cold-water-soluble powder, with an adhesive coating on both sides of the air-permeable membrane layer (not shown).

In one embodiment, a thin film culture plate device can be made by producing a liquid coating mixture, coating the liquid coating mixture onto a substrate, drying the coated substrate and, optionally, attaching a cover sheet according to processes described in U.S. Pat. No. 4,565,783, for example. An exemplary device of this embodiment is shown in FIG. 4.

FIG. 4 illustrates an embodiment of a thin film culture device 410 suitable for use with the media of the present invention. The process for making the device is described in U.S. Pat. No. 4,565,783, which is incorporated herein by reference in its entirety.

The thin film culture device 410 includes a body member having a self-supporting, waterproof substrate 412. Substrate 412 is preferably a relatively stiff material made of a waterproof material that does not absorb water such as polyester, polypropylene, or polystyrene. Other suitable waterproof materials include substrates such as paper containing a waterproof polyethylene coating. The upper surface of substrate 412 is coated with a liquid composition, which is then dried to provide a dry coating 417 on substrate 412. The dry coating 417 comprises a cold-water soluble gelling agent as described herein and may also include a nutrient, a selective agent, an indicator or a combination of any two or more of the foregoing. The liquid composition used to produce the dry coating 417 may be readily dried by heating liquid composition in an oven at about 220° F. until essentially all of the water in the composition has evaporated. If the composition is heated after the water has evaporated, however, certain components of the composition (e.g., nutrients, indicators) may begin to degrade.

A layer of adhesive (not shown) may be coated on substrate 412. The adhesive may serve to hold the dry coating 417 to the substrate 412. The adhesive should be sufficiently transparent when hydrated to allow viewing of bacterial colonies growing on the surface of the coated substrate 412. The adhesive should also be coated on the substrate 412 in a thickness which allows the substrate to be uniformly coated with dry coating 417 without completely embedding the coating in the adhesive.

A foam spacer 418 having a circular opening in the foam is adhered to the medium coated surface of substrate 412. The foam spacer which covers the periphery of substrate 412 defines the area which is to be inoculated with a sample and serves to prevent the sample from leaking from the substrate. In an alternate embodiment, device may not include a sample-containing foam layer. In this device, the amount of sample is contained on the substrate by the components of the medium alone.

A cover sheet 422 is attached to an edge of an upper surface of the foam spacer 418. Cover sheet 422 is preferably made of a transparent film or sheet material in order to facilitate counting of bacterial colonies present on the substrate. In addition, cover sheet 422 is preferably impermeable to bacteria and water vapor in order to avoid the risk of contamination and deterioration of the components. A preferred material for use as a cover sheet 422 is biaxially-oriented polypropylene. Optionally, the coversheet 422 may be coated with a layer of adhesive, which may be coated with a dried composition (e.g., powders) comprising a gelling agent, nutrients, selective agents, an indicator (e.g., a DNase indicator system), or a combination of any two or more of the foregoing (not shown).

In use, a predetermined amount of inoculum, typically about one milliliter of a liquid inoculum, is added to the device illustrated in FIG. 4 by pulling back cover sheet and distributing an aqueous test sample or water onto the dry coating 417. The inoculum may optionally comprise a nutrient, a selective agent, an indicator or a combination of any two or more of the foregoing. Cover sheet 422 is then replaced over the coating 417 and the inoculum is evenly spread inside the circular opening of the foam spacer 418. A convenient tool to do this is a weighted circular template. As the inoculum contacts and is spread on coating 417, the coating hydrates to form a gel. Nutrients present in the gel can support the growth of microorganisms. The inoculated device is then incubated for a predetermined time after which the number of bacterial colonies growing on the substrate may be counted through the transparent cover sheet 422.

The coating mixture used to form the dry coating 417 of device 410 can comprise the DNase indicator system and, optionally, a culture medium, an indicator reagent, a selective agent or any combination of two or more of the foregoing. A preferred coating mixture, when coated, dried, and rehydrated with an appropriate volume of sample, comprises the nutrient medium and the DNase indicator system shown in Table 1.

TABLE 1

Composition of an exemplary nutrient medium.

| Ingredient | Amount (milligrams/mL) |
| --- | --- |
| Tryptone | 6.6 |
| Yeast Extract | 4.6 |
| Dextrose | 0.9 |
| Sodium pyruvate | 13.2 |
| K$_2$HPO$_4$ | 3.0 |
| KH$_2$PO$_4$ | 0.6 |
| Methyl green | 0.02 |
| λ-carrageenan | 0.1 |

TABLE 1-continued

Composition of an exemplary nutrient medium.

| Ingredient | Amount (milligrams/mL) |
| --- | --- |
| DNA | 2.0 |
| Guar gum | 10 |

The culture medium of the present invention may include nutrients, salts and ions generally suitable to promote the growth of target (i.e., DNase-producing) microorganisms when the culture medium is inoculated with a sample suspected of containing microorganisms. Culture media containing additives such as, for example, nutrients, salts, ions, selective agents, indicators, and the like can be tested with known DNase-producing organisms to determine that the additive promotes the growth of the target microorganism, inhibits the growth of non-target microorganisms, and/or does not interfere with the DNase indicator system. The culture medium also may include one or more gelling agents. Suitable nutrients, salts, ions, and gelling agents are described in U.S. Pat. No. 5,443,963. The culture medium of the present disclosure can include at least one selective agent that selects for growth of certain DNase-producing microorganisms (e.g. *Staphylococcus, Bacillus, Streptococcus, Vibrio, Branhamella* and/or *Serratia* species)

The selection of target microorganisms may include inhibiting the growth of non-non-target microorganisms, promoting the growth of non-target microorganisms, or both. Promoting the growth of target microorganisms may be provided by the at least one first selective agent either directly (e.g., a nutrient that can be used by target microorganisms and not by other microorganisms), indirectly (e.g., by reducing competition for nutrients by inhibiting non-target microorganisms), or both directly and indirectly.

Any element, radical, ion, or compound that selects for the growth of target microorganisms may be suitable for use as a selective agent. For example, suitable selective agents for staphylococcal target microorganisms include but are not limited to lithium chloride, aztreonam, potassium tellurite, sodium chloride, nalidixic acid, colistin methanesulfonate, glycine-hydrochloride, potassium thiocyanate, sodium azide, polymyxin B, sulfamethazine, an antibiotic, and any combination of two or more of the foregoing.

Certain selective agents may not only select for the growth of staphylococci, but also may differentially select for growth of *S. aureus* over other staphylococci under certain conditions. For example, a culture medium that includes potassium tellurite, lithium chloride, and egg yolk is capable of selectively differentiating *S. aureus* from all other bacterial species. Egg yolk is commercially available either as an emulsion or in a dehydrated form.

A dry culture medium according to the present invention may be applied to one or more surfaces of a thin film culture device in the following manner. The components of the culture medium may be dissolved in a solvent. The resulting solution may then be coated onto one or more surfaces of the device. The coating is then allowed to dry, leaving dried culture medium on the surfaces of the device that had been coated with the culture medium solution. The coating may be dried in any suitable manner including, but not limited to, air drying and heating.

The quantity of each component of the dry culture medium is at least partially determined by at least two factors: (1) the concentration of that component in the culture medium solution, and (2) the amount of the solution coated onto a given surface area of the culture device (the coating weight). Suitable coating weights may range from about 0.45 mg/cm² to about 2.5 mg/cm². In some embodiments, the culture medium nutrients may be coated separately from the indicators. In such embodiments, the coating weight for the culture medium nutrients may range from about 1.6 mg/cm² to about 2.5 mg/cm². In one embodiment, the coating weight of the nutrient coating is about 2.1 mg/cm². The coating weight for the indicator coating may range from about 0.45 mglcm2 to about 0.84 mglcm2. In one embodiment, the coating weight of the indicator coating is about 0.62 mg/cm2.

The amount of the selective agent included in the culture medium may depend, in part, upon the particular selective agent or combination of selective agents chosen for use in a particular culture medium. For example, in one embodiment, the culture medium includes lithium chloride, aztreonam, and potassium tellurite as selective agents. In the context of the coating weights described above for a nutrient coating, lithium chloride may be included in the coating solution in an amount that ranges from about 1 g/L to about 15 g/L. In one embodiment, the coating solution includes 10 g/L of lithium chloride before being coated onto the culture device. Similarly, aztreonam may be included in an amount that ranges from about 0.001 g/L to about 0.015 g/L. In one embodiment, the coating solution includes 0.01 g/L of aztreonam. Potassium tellurite may be included in an amount that ranges from about 0.05 g/L to about 0.19 g/L. In one embodiment, the culture medium includes 0.16 g/L of potassium tellurite.

In any one of the above embodiments, the gelling agent is hydrated (e.g., by an aqueous solution comprising the sample) to form a hydrogel. The hydrogel can be any suitable hydrogel that limits the diffusion of DNase enzyme in an aqueous solution but does not substantially inhibit the activity of DNase enzyme activity. Non-limiting example of suitable hydrogels include agar, agarose, gelatin, natural gums (guar gum, locust bean gum, xanthan gum, and the like) and derivatives and combinations thereof.

Although the embodiments illustrated in FIGS. 1-4 have a cover sheet attached to the device, it is also contemplated within the scope of the invention that the powder-containing embodiments may be uncovered and simply placed in a sterile environment during storage and incubation.

Detection Articles:

The present disclosure includes articles for the detection of DNase activity. The detection articles comprise a body member comprising a self-supporting substrate having upper and lower major surfaces. The articles further comprise a coating comprising a cold water-soluble gelling agent and a DNase indicator system comprising DNA and methyl green. The coating can be prepared and adhered uniformly onto a portion of at least one surface of the substrate using processes similar to those described in U.S. Pat. No. 6,022, 682, which is incorporated herein by reference in its entirety.

Figure 5:
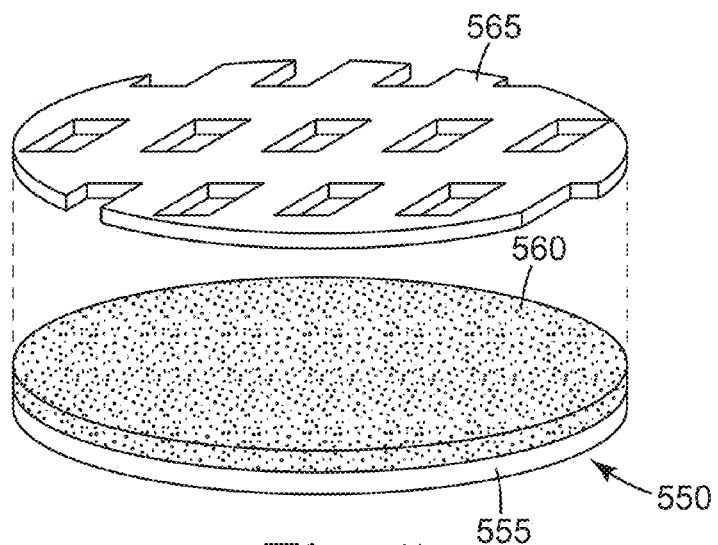
FIG. 5 is a top perspective view, partially exploded, of an embodiment of a detection article with a spacer in accordance with the present disclosure.

FIG. 5 shows one embodiment of a detection article 550 according to present invention in partially exploded, perspective view. The article shown in FIG. 5 has a generally disk-like shape, but the article may have any shape desired for a particular application. The article 550 comprises a solid support 555, detection layer 560 coated onto the upper major surface of the solid support 555, and, in exploded view, optional protective material 565, shown as a grid. The protective material 565, if present, can be removed to reveal a surface of the detection layer 560 for placement against a surface comprising a sample.

In general, the preparation of the article 550 involves preparing a solution containing appropriate amounts of ingredients selected for inclusion in the article, including DNA, methyl green, and a cold water-soluble gelling agent, cooling the solution and then coating the solution onto a solid support 555. The coated support is then dried to solidify the coated solution. To illustrate one preferred, but nonlimiting, embodiment, a solution containing 2 g/L salmon sperm DNA, 0.02 g/L methyl green, and 1% (weight/volume) guar gum is coated onto a 0.18 mm polyester film solid support, and then dried 2-10 minutes at 200° F. The resultant dried coating may be of any desired thickness, but preferably has a thickness of about 0.12-0.25 mm. The ingredients, and the amounts thereof, may be selected such that the article is relatively rigid or flexible, depending on what is desired for a particular application.

The solid support 555 may be a polymer film, such as a polyester film. The solid support 555 may be derived from molds for providing molded articles after drying, or the solid support may be derived from a sheet material, allowing for the cutting, or punching, of articles of desired size or shape following coating and drying. The material used for the solid support 555 may be selected to impart any degree of rigidity or flexibility to the article 550. In addition, the article 550 may be prepared in any shape or thickness, depending on what is desired for a particular application.

The solid support preferably is transparent or at least translucent, to allow the viewing of color changes that develop in the article in use. The solid support also provides stability to detection layer and protects it from damage.

The solid support may be selected such that it is peelable from the detection layer, leaving the detection layer free for use in testing without the solid support. For example, where a polyester film is used as the solid support, the solid support may be peelable from the detection layer when the layer becomes hydrated during use.

The protective material 565 may be placed adjacent to an exposed surface of the detection layer. For example, where a solid support is adjacent to one surface of the detection layer, the protective material may be adjacent to the opposite surface. The protective material may be a polymer film or grid (e.g., a scrim) that protects the article in storage and transport, and may preferably operate as a spacer between detection layers, to separate the articles, which can be hygroscopic after drying, from one another and permit stable storage and longer shelf-life.

The protective material is selected such that it is peelable or removable from the surface of the article prior to use. Suitable materials for use as the protective material are known in the art. As mentioned above, the article of the invention may be of any desired thickness, shape, or rigidity, and, if present, the solid support may be of any desired thickness and may be selected to impart any desired degree of rigidity or flexibility.

The article preferably may also include other constituents, such as calcium chloride (for example, to detect thermonuclease activity), sodium chloride (to provide appropriate ionic strength), or a buffer system (to control pH at which the DNase reaction occurs), such as Tris hydrochloride/Tris base.

The article of the invention may be prepared from solutions of varying pH. As such, the article can contain reagents such that DNase activity will occur at a selected pH. For example, an article in accordance with a preferred embodiment of the invention may be made from a pH 7.3 solution. Alternatively, an article in accordance with the invention may be made from a pH 9.0 solution.

Samples

Suitable samples may be derived from any source, such as a physiological fluid, e.g., blood, saliva, ocular lens fluid, synovial fluid, cerebral spinal fluid, pus, sweat, exudate, urine, mucus, feces, lactation milk, or the like. Further, the test sample may be derived from a body site, e.g., wound, skin, nares, scalp, nails, etc.

Samples of particular interest include mucus-containing samples, such as nasal samples (from, e.g., anterior nares, nasopharyngeal cavity, nasal cavities, anterior nasal vestibule, etc.), as well as samples from the outer ear, middle ear, mouth, rectum, vagina, or other similar tissue. Examples of specific mucosal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces, floors, walls, instruments, bedding), and the like. Samples can also include cultured cells.

Various patient sampling techniques for the detection of microbes, such as *S. aureus*, on surfaces are known. Such sampling techniques are suitable for the methods of the present invention as well. For example, it is common to obtain a sample from wiping the nares of a patient. A particularly preferred sampling technique includes the subject's (e.g., patient's) anterior nares swabbed with a sterile swab or sampling device. For example, one swab is used to sample each subject, i.e., one swab for both nares. The sampling can be performed, for example, by inserting the swab dry or pre-moistened with an appropriate solution into the anterior tip of the subject's nares and rotating the swab for one or more complete revolutions along the nares' mucosal surface.

A wide variety of swabs or other sample collection devices are commercially available, for example, from Puritan Medical Products Co. LLC, Guilford, Me., under the trade designation PURE-WRAPS or from Copan Diagnostics, Inc. Corona, Calif., under the trade designation ESWAB, or from microRheologics, S.r.l., Brescia, IT, under the trade designation FLOCKEDSWAB. A sample collection means such as that disclosed, for example, in U.S. Pat. No. 5,879,635 (Nason) can also be used if desired. Swabs can be of a variety of materials including cotton, rayon, calcium alginate, Dacron, polyester, nylon, polyurethane, and the like.

The sample collection device (e.g., swab) can then be cultured directly, analyzed directly, or extracted (e.g., by washing, elution by vortexing) with an appropriate solution. Such extraction (i.e., elution) solutions typically include water and can optionally include a buffer and at least one surfactant. An example of an elution buffer includes, for example, phosphate buffered saline (PBS), which can be used in combination, for example, with TWEEN 20 or PLURONIC L64. The test sample (e.g., liquid) may be subjected to treatment prior to further analysis. This includes concentration, precipitation, filtration, centrifugation, dialysis, dilution, inactivation of natural components, addition of reagents, chemical treatment, etc.

Capture Particles

Culture devices of the present disclosure can be used with capture particles to detect microorganisms in a sample (e.g., liquid suspension). Preferably, capture particles are dimensioned to allow them to be placed into the culture devices of the present invention and remain in the culture devices during the incubation period for a sufficient period to allow for at least one cell division of the target microorganism. Placing the capture particle into the culture device can bring the capture particle in contact with a gelling agent and/or a nutrient medium, if present, in the culture device, allowing microorganisms to grow and/or proliferate. In some embodiments, the culture device is hydrated (e.g., inoculated with a sterile liquid or an unknown liquid sample) before the capture particle is placed into the culture device. In some embodiments, the culture device is hydrated after the capture particle is placed into the culture device.

Suitable capture particles include a particle, or a plurality of particles. The particles can include a means for coupling the particle to microorganisms. Nonlimiting examples of particles include microspheres, microbeads, nanobeads, and the like. Such particles can be resin particles, for example, agarose, latex, polystyrene, nylon, polyacrylamide, cellulose, polysaccharide, or a combination thereof, or inorganic particles, for example, silica, aluminum oxide, or a combination thereof. Such particles can be magnetic, paramagnetic, superparamagnetic, or non-magnetic. Such particles can be colloidal in size, for example about 100 nm to about 10 microns (μm). Nonlimiting examples of such particles include superparamagnetic polymer particles sold under the trade names DYNABEADS (Invitrogen, Inc., Carlsbad, Calif.) and BIO-ADEMBEADS (Ademtech, Pessac, France).

There are a variety of means for coupling capture particles to a microorganism. In some embodiments, the means for coupling the capture particle to the microorganism can include surface molecules or properties that promote non-specific adsorption. For example, at least a portion of the capture particle can have molecules on its surface that, under the proper conditions (e.g., high pH or low pH), become positively- or negatively-charged and nonspecifically adsorb to complementary-charged molecules associated with the surface of a microorganism.

Additionally, or alternatively, at least a portion of the capture particle (e.g., a polystyrene particle) can have a hydrophobic surface which nonspecifically adsorbs to hydrophobic molecules associated with the surface of a microorganism. In some embodiments, the means for coupling a capture particle to a microorganism may comprise a molecule that specifically binds to a microorganism through a receptor-ligand interaction. Such specific receptor-ligand interactions are well known in the art and include interactions between, for example, antibodies or antibody fragments and their corresponding antigens, lectins and their corresponding carbohydrate binding partner, bacteriophage proteins or fragments and their corresponding phage receptors, and the like.

Methods for Detecting DNase Activity in a Sample

The present disclosure provides a method for detecting a discrete source of DNase enzyme activity in a sample. "Discrete source of DNase enzyme activity", as used herein, refers to a source of DNase activity in which a portion of the sample has a concentration of DNase activity that is measurably distinct from at least one other portion of the sample. In some embodiments, the discrete source of DNase activity can be a cell (e.g., a plant cell, an animal cell, or a microorganism) of a group of cells (e.g., a portion of biological tissue, a colony of microorganisms).

The DNase enzyme activity is detected with the use of an indicator system comprising DNA and methyl green, both in sufficient quantities to detect a green color due to the formation of a complex between the DNA and the methyl green. In the presence of a source of DNase enzyme activity, the DNA molecules are digested and, thus, the DNA-methyl green complex disintegrates and becomes colorless.

The method for detecting a discrete source of DNase activity comprises providing a hydrogel including a DNase indicator system, and a sample suspected of containing a discrete source of DNase activity.

The DNase indicator system comprises DNA and methyl green. The DNA and methyl green are both in sufficient quantities to exhibit a green color due to the formation of a complex between the DNA and the methyl green. The concentration of methyl green used in the art provides enough color contrast to visually detect the decolorized zones surrounding the DNase-producing microbial colonies. However, that concentration of methyl green is shown herein to inhibit the growth of at least some microorganisms.

The DNA in the DNase indicator system can be the sodium salt of DNA from salmon testes (available from Sigma Chemical Co., St. Louis, Mo.) or from heimfish sperm (available from Acros Organics, Geel, Belgium) at a concentration in the hydrogel of about 2.0 g/L, for example.

In some embodiments, the DNase indicator system can be detected manually. For manual detection, the article or device containing the DNase indicator system is observed visually by a technician, who determines whether a source of DNase activity (e.g., a colony of microorganisms) is present in the article or device. In some embodiments of the present disclosure, the inventive method includes the use of relatively low concentrations of methyl green in the hydrated articles or devices comprising the DNase indicator system. In these embodiments, there is significantly less inhibition of the growth of microorganisms and, surprisingly, there remains enough color contrast to visually detect the DNase-producing microorganisms. In certain manual detection embodiments, the methyl green in the hydrated article or device can be, for example, the zinc chloride salt of methyl green at a concentration of at least about 5 µg/mL to no more than 49 µg/mL. In certain manual detection embodiments, the methyl green in the hydrated article or device comprising the sample can be the zinc chloride salt of methyl green at a concentration of at least about 5 µg/mL to about 40 µg/mL. In certain manual detection embodiments, the methyl green in the hydrated article or device comprising the sample can be the zinc chloride salt of methyl green at a concentration of at least about 5 µg/mL to about 30 µg/mL. In certain manual detection embodiments, the methyl green in the hydrated article or device comprising the sample can be the zinc chloride salt of methyl green at a concentration of at least about 5 µg/mL to about 20 µg/mL. In certain manual detection embodiments, the methyl green in the hydrated article or device comprising the sample can be the zinc chloride salt of methyl green at a concentration of at least about 5 µg/mL to about 10 µg/mL. In certain manual detection embodiments, the methyl green in the hydrated article or device comprising the sample can be the zinc chloride salt of methyl green at a concentration of about 5 µg/mL, about 10 µg/mL, about 20 µg/mL, about 30 µg/mL, about 40 µg/mL, or about 45 µg/mL.

Additionally, or alternatively, the DNase indicator system can be analyzed electronically, using an imaging system as described herein. The color contrast between the DNA-methyl green complex and the hydrolyzed DNA-methyl green complex can be substantially enhanced by using an imaging process that includes, for example, a process of illuminating the indicator system with selected wavelengths of light (i.e., red wavelengths), imaging a hydrogel comprising the indicator system, analyzing an image of the hydrogel comprising the indicator system, or by a combination of two or more of the foregoing processes. In certain electronic detection embodiments, the methyl green in the hydrated article or device comprising the sample can be, for example, the zinc chloride salt of methyl green at a concentration of at least about 5 µg/mL to about 100 µg/mL. In certain electronic detection embodiments, the methyl green in the hydrated article or device comprising the sample can be the zinc chloride salt of methyl green at a concentration of at least about 5 µg/mL to about 60 µg/mL. In certain electronic detection embodiments, the methyl green in the hydrated article or device comprising the sample can be the zinc chloride salt of methyl green at a concentration of at least about 5 µg/mL to about 40 µg/mL. In certain electronic detection embodiments, the methyl green in the hydrated article or device comprising the sample can be the zinc chloride salt of methyl green at a concentration of at least about 5 µg/mL to about 20 µg/mL. In certain electronic detection embodiments, the methyl green in the hydrated article or device comprising the sample can be the zinc chloride salt of methyl green at a concentration of at least about 5 µg/mL to about 10 µg/mL. In certain electronic detection embodiments, the methyl green in the hydrated article or device comprising the sample can be the zinc chloride salt of methyl green at a concentration of about 5 µg/mL, about 10 µg/mL, about 20 µg/mL, about 30 µg/mL, about 40 µg/mL, or about 45 µg/mL.

In methods that include either manual or electronic analysis, the methods further comprise contacting, for a predetermined time, the source of DNase activity and a hydrogel comprising the DNase detection system under conditions suitable to permit DNase activity. DNase enzymes are known in the art, as are the conditions suitable to permit DNase enzyme activity. Certain DNase enzyme (e.g., DNase I) activities are facilitated by divalent cations, such as, for example, calcium and magnesium. The divalent cations may be added to the hydrogel and/or may be included in a nutrient medium, if present, in the hydrogel or the sample. In general, DNase enzymes have optimal activity at about a neutral pH. In certain embodiments, the pH is about 6.5 to about 8.0. In general, the rate of an enzyme reaction (e.g., DNase enzyme activity reaction) increases at higher temperatures. Thus, the DNase activity can be contacted with the hydrogel at relatively lower temperatures (e.g., ambient temperature) or at elevated temperatures (e.g., 30-45° C.). Typically, the amount of time required to detect the DNase activity will be shorter when the reaction is incubated at elevated temperatures. During the contact period, the hydrogel may be held in a container to limit the loss of moisture from the hydrogel. Suitable containers include, for example, a petri dish, a thin film culture plate device, or a humidified beaker.

In some embodiments, the method further comprises obtaining an image of the hydrogel with the imaging system. The imaging system comprises a processor and an imaging device. In some embodiments, the imaging device comprises a line-scanner or an area scanner (e.g., a camera). The imaging device can include a monochromatic (e.g., black-and-white) or a polychromatic (e.g., color) scanner. Advantageously, monochromatic imaging systems can provide higher resolution images, which may improve the accuracy of the result and/or reduce the time necessary to determine the presence of DNase in a sample.

In some embodiments, the imaging system comprises an illumination system. The illumination system may include at least one source of broad-spectrum visible light (e.g., a "white" light). In some embodiments, the illumination system may include at least one source of narrow-spectrum visible light (e.g., a light-emitting diode that emits a relatively narrow bandwidth of visible light such as, for example, red, green, or blue light). In certain embodiments, the illumination system may include a source of narrow-spectrum visible light (e.g., a light-emitting diode) with a light emission peak at about 633 nm.

The image can be obtained from light reflected by the hydrogel or the image can be obtained from light transmitted through the hydrogel. Suitable imaging systems and corresponding illumination systems are described, for example, in International Patent Publication No. WO 2005/024047 and U.S. Patent Application Publication Nos. US 2004/0101954 and US 2004/0102903, each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Synbiosis (Cambridge, U.K.)

In some embodiments, obtaining an image comprises obtaining a wavelength-biased image. For example, the imaging system can include a bias filter that biases the light collected by the imaging device. Filter elements are known in the art and include both "cut-off" filters (i.e., filters that allow the passage of light wavelengths either above or below a certain specified wavelength) and "band-pass" filters (i.e., filters that allow the passage of light wavelengths between certain specified upper and lower limits). A bias filter can be positioned between the illumination source and the hydrogel. Alternatively or additionally, a bias filter can be positioned between the hydrogel and the imaging device.

In certain preferred embodiments, obtaining an image comprises obtaining an image using a bias filter that selectively allows the passage of red wavelengths. In some embodiments, obtaining an image comprises using a bias filter that selectively allows the passage of wavelengths from about 620 nm to about 740 nm.

Figure 6:
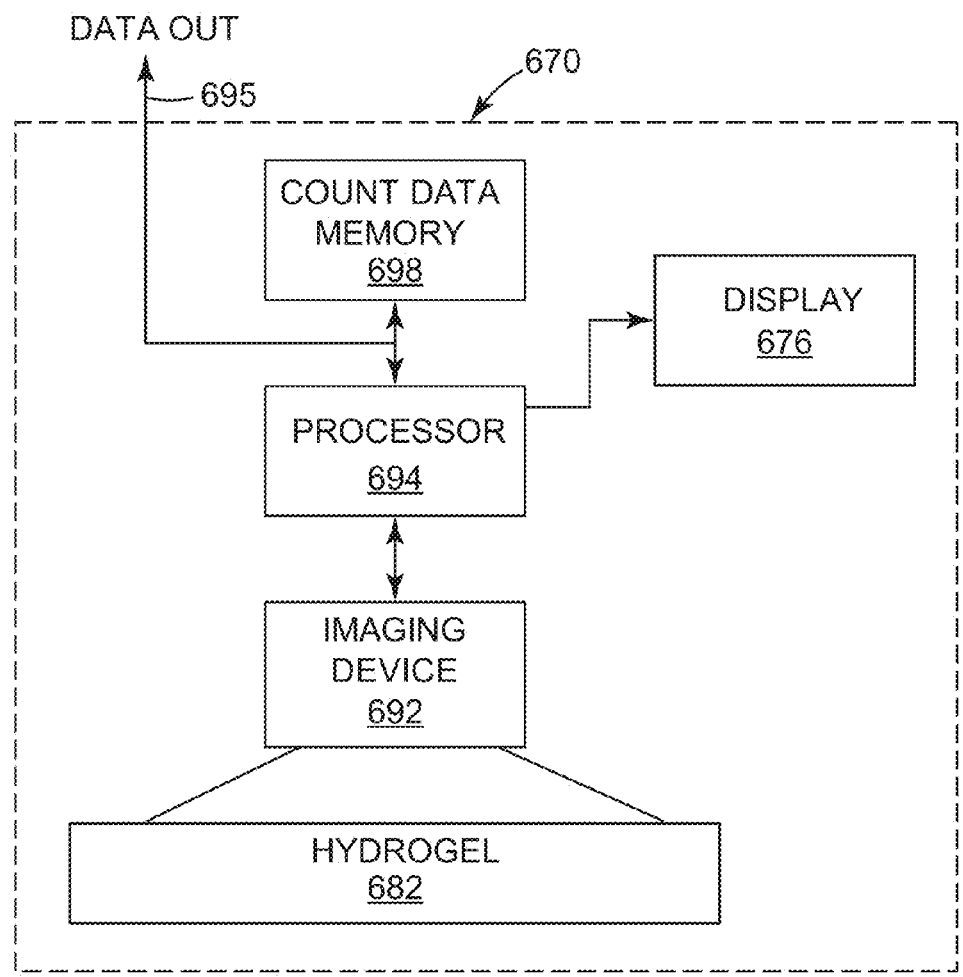
FIG. 6 is a block diagram of one embodiment of a detection system according to the present disclosure.

FIG. 6 is a block diagram illustrating internal operation of an imaging system 670. As illustrated in FIG. 6, a hydrogel 682 is positioned in a focal plane (e.g., on a platform, not shown) within imaging system. In accordance with the invention, imaging device 692 may include multi-color illumination systems (not shown) for front and/or back illumination of hydrogel 682, as well as a monochromatic line or area scanner that captures an image of the hydrogel 682. In some embodiments, for example, imaging device 692 may take the form of a two-dimensional, monochromatic camera.

In general, imaging device 692 captures images of hydrogel 682, or at least a portion thereof, during illumination of the hydrogel with one or more different illumination colors. In some embodiments, multiple images of the same hydrogel 682 can be generated with various illumination durations or intensities and one or more of the multiple images can be selected for analysis. In some embodiments, selective illumination of a first side and a second side of the hydrogel 682 can be used to generate multiple images of the hydrogel and one or more of the images can be selected for analysis. Selection of an image for analysis can be based on, for example, the color contrast and/or object resolution properties of the individual images. Processes for determining the color contrast and object resolution properties of an image are known in the art and are disclosed in, for example, U.S. Pat. No. 6,243,486, which is incorporated herein by reference in its entirety.

A processor 694 controls the operation of imaging device 692. Also shown in FIG. 6 is optional display 676, which can receive an image from the processor 694 for visual review by an operator. In operation, processor 694 controls imaging device 692 to illuminate the hydrogel 682 and obtain an image. Processor 694 receives image data representing the scanned image from imaging device 692. In some embodiments, processor 694 can select an image, from multiple images, for analysis and/or display. Processor 694 analyzes at least one image of hydrogel 682 and may produce an analytical result, such as a count of discrete sources of DNase activity or a presence/absence result. The analytical result (e.g., a qualitative or quantitative result) can be displayed on display 676, stored in optional data storage memory 698, or retrieved by a host computer (not shown) via optional communication port 695

The method further comprises detecting deoxyribonuclease activity in the hydrogel. Detecting deoxyribonuclease activity in the hydrogel comprises analyzing the image of the hydrogel. In the presence of a discrete source of DNase enzyme activity, the DNA molecules are digested and, thus, the DNA-methyl green complex disintegrates and, thereby, decolorizes. Because the diffusion of DNase activity away from the discrete source is limited by the hydrogel, the DNase activity associated with a discrete source (e.g., a cell or colony of cells) results in the formation of a relatively less-colored zone adjacent to the discrete source of DNase activity (i.e., there is less green color adjacent to the source of DNase activity than other areas of hydrogel that are not in contact with DNase activity). Typically, a relatively colorless zone will appear in the hydrogel surrounding the discrete source of DNase activity. Thus, analyzing the image of the hydrogel can comprise analyzing the image for zones of the hydrogel that have relatively less green color than at least one other portion of the hydrogel. In some embodiments, analyzing the image of the hydrogel can comprise comparing the amount of green color in one or more areas (or the entire area) of the hydrogel to another image of a corresponding hydrogel without DNase activity (i.e., a negative control).

Analyzing the image of the hydrogel can comprise using a system to detect color and/or varying shades of a color (e.g., red, green, blue, gray) in an image. Suitable image analysis systems include the image analysis systems described in, for example, U.S. Pat. Nos. 5,448,652; 6,243,486; and 6,153,400; each of which is incorporated herein by reference in its entirety.

In certain embodiments, analyzing the image of the hydrogel comprises analyzing selected wavelengths of the image. In some embodiments, the image may be a color image collected by illuminating the hydrogel with a source of broad-spectrum visible light (e.g., a "white" light). In some embodiments, the image may be a color image collected by illuminating the hydrogel with a plurality of sources of relatively narrow-spectrum visible light (e.g., a combination of light-emitting diodes that each emits a relatively narrow bandwidth of visible light such as, for example, red, green, or blue light). In some embodiments, the image may be a composite image made by combining two or more images collected while illuminating the hydrogel with two or more different sources of relatively narrow-spectrum visible light (e.g., red, green, or blue light). In some embodiments, the image may be an image collected while illuminating the hydrogel with a source of relatively narrow-spectrum visible light (e.g., red light). In these embodiments, certain wavelengths of the image can be selected for displaying or printing an image and/or image analysis. In some embodiments, the wavelengths selected for analyzing the image can be wavelengths in the red (e.g., wavelengths about 625 nm to about 740 nm). In some embodiments, the wavelengths selected for analysis are wavelengths about 630 nm to about 670 nm. In some embodiments, the wavelengths selected for analysis are wavelengths about 630 nm to about 650 nm.

The wavelengths can be selected, for example, by using a computer program that electronically selects a predetermined range of wavelengths in the image for display, printing, and/or analysis. Any suitable computer program can be used to select a predetermined range of wavelengths in an image. Non-limiting examples of suitable computer programs include PHOTOSHOP CS4 software, available from Adobe Systems, Inc. (San Jose, Calif.) and IMAGE-PRO Plus software, available from Media Cybernetics (Silver Springs, Md.).

In certain embodiments, wherein the image of the hydrogel has been obtained and/or analyzed in a manner that biases the collection in the image of red wavelengths either transmitted through and/or reflected by the hydrogel, the contrast between the green-colored DNA-methyl green complex and the colorless, depolymerized DNA is significantly enhanced. Thus, in these embodiments, DNase activity is detectable at an earlier time than in comparable methods that do not bias the wavelengths of the image that is collected. Additionally, methods that bias the collection of red wavelengths either transmitted through and/or reflected by the hydrogel permit the detection of lower amounts of DNase activity than in comparable methods that do not bias the wavelengths of the image that is collected.

Methods for Detecting a Microorganism in a Sample

The present disclosure provides a method for detecting a microorganism in a sample. In some embodiments, the method comprises providing a dry composition and a sample suspected of containing a microorganism. The dry composition comprises a cold water-soluble gelling agent and an indicator system including methyl green and DNA, as described herein. Optionally, the dried hydrogel composition further comprises a nutrient, a selective agent, an antibiotic, an indicator, or a combination of any two or more of the foregoing. The method further comprises contacting a predetermined volume of aqueous liquid comprising the sample with the dried hydrogel to form a rehydrated hydrogel, incubating the rehydrated hydrogel for a period of time, and detecting a microorganism.

The dry composition is placed on or into an article (e.g., a beaker, a flask, a tube, a Petri dish) suitable to hold the dry composition when the composition is in a dry and/or a hydrated state. In some embodiments, the dry composition is coated onto a substrate to form a detection article. In some embodiments the dry composition is powder-coated onto an adhesive-coated substrate and the dry composition adheres to the adhesive. In some embodiments, the composition is hydrated, coated onto a substrate, and the hydrated composition is subsequently substantially dried to form the dry composition. The substrate onto which the hydrated composition is coated may comprise an adhesive to which the dried composition adheres. Processes for coating a substrate and, optionally, drying the coating on the substrate to form a detection article are described, for example, in U.S. Pat. Nos. 4,565,783; Re. 35,286; and 6,022,682, each of which is incorporated herein by reference in its entirety.

The dry composition is contacted with a predetermined volume (e.g., 1 mL, 3 mL, 5 mL) of aqueous liquid comprising the sample. The sample may comprise an aqueous liquid (e.g., a sample of water or milk). The sample may comprise a liquid or a solid suspended in an aqueous liquid (e.g., water or an aqueous buffer such as, for example, phosphate buffered saline or Butterfield's buffer). Optionally, a nutrient, a selective agent, an indicator, or any combination of two or more of the foregoing can be added to the aqueous liquid comprising the sample before and/or after the aqueous liquid contacts the dry composition. In some embodiments, the selective agent comprises an antibiotic such as, for example, a cephalothin, cefazolin, cephradine, cephalexin, cefadroxil, cefamandole, cefoxitin, cefaclor, cefuroxime, cefuroxime axetil, loracarbef, cefonicid cefotetan, ceforanide, cefotaxime, cefpodoxime proxetil, ceftizoxime, cefixmeceftriaxone, cefoperazone, ceftazidime, moxlactam, cefepime, cefpirome, and oxacillin. The aqueous liquid comprising the sample hydrates the dry composition to form a hydrogel.

The hydrogel is incubated for a period of time during which the microorganisms may grow and/or a DNase activity associated with a microorganism, if present, may interact with the DNase indicator system. The temperature and duration of the incubation step can be selected according to the microorganism to be detected. In general, bacterial cultures are incubated at 22-45° C. for 16-48 hours. In some embodiments, the cultures are incubated at 30-37° C. for 24-48 hours. Slow-growing bacteria may be incubated for longer periods. In general, fungal cultures (e.g. yeast or filamentous fungi) are incubated at 22-37° C. for 1-5 days. It is well within the skill of an ordinary person in the art to determine the incubation conditions for a given microorganism grown in a given nutrient medium. In some embodiments, a microorganism may be detected by its interaction with the DNase indicator system, as described herein. In some embodiments, a microorganism may be detected by its interaction with an additional indicator, if present in the hydrogel. In some embodiments, a microorganism can be identified as a certain type (e.g., DNase-positive, DNase-negative, coliform, antibiotic-resistant, etc.) by its interaction with the DNase indicator system, a selective agent, and/or one or more additional indicator systems in the hydrogel. In some embodiments, the number of microorganisms interacting with one or more indicator system can be counted to indicate the number of microorganisms present in the original sample.

Detecting a microorganism can comprise detecting colony. Methods of detecting colonies in nutrient media for culturing microorganisms is well known in the art and includes, for example, detecting colonies visually or microscopically. Additionally, or alternatively, detecting a microorganism can include detecting an indicator associated with a microorganism or group of microorganisms. Suitable indicators for detecting microorganisms are known in the art and include, for example, chromogenic or fluorogenic oxidation-reduction indicators (e.g., triphenyl tetrazolium choride), chromogenic or fluorogenic enzyme substrates (e.g., 5-bromo-4-chloro-3-indolyl phosphate, 4-umbelliferyl-beta-D-glucopyranoside), or pH indicators (e.g., chlorophenol red, bromthymol blue). Additionally, or alternatively, detecting a microorganism can include detecting DNase activity associated with a DNase-producing microorganism. The present disclosure provides devices and methods for the detection of antibiotic-resistant microorganisms. Because *Staphylococcus aureus* is known to produce DNase activity, the present disclosure provides devices and methods to detect and distinguish antibiotic-resistant *S. aureus* (e.g., Methicillin-resistant *S. aureus*, or MRSA).

Methods of the present disclosure can provide for early detection of a DNase-producing microorganism. For example, a method can comprise inoculating a culture medium comprising a DNase indicator system including 2 mg/mL DNA and 20 µg/mL methyl green. After incubation under suitable conditions (e.g., 37 degrees C.), an image of the culture medium can be obtained using, for example, a NIKON E8400 digital camera (Nikon, Inc., Melvelle, N.Y.) and the images can be analyzed using, for example, IMAGE-PRO Plus software (Media Cybernetics, Silver Springs, Md.). Viewing the full-color images, colonies of DNase-producing microorganisms can be detected after about 12.5 hours of incubation. Viewing the red channel images, colonies of DNase-producing microorganisms can be detected after about 11.5 hours of incubation.

In some embodiments, the method further comprises providing an imaging system, and obtaining an image of the hydrogel, wherein detecting a microorganism comprises displaying, printing, or analyzing the image of the hydrogel. Suitable imaging systems and conditions are described herein. In some embodiments, the image of the hydrogel is displayed such that the operator can view the image and detect the presence and/or number of DNase-producing microorganisms in the sample or the absence and or number of DNase-producing microorganisms in the sample. In some embodiments, the image is analyzed by a processor, which detects the presence and/or number of DNase-producing microorganisms in the sample or the absence and or number of DNase-producing microorganisms in the sample.

Kits of the Invention

Kits provided by the present invention include two or more parts. One part includes a detection article or a culture device comprising a cold water-soluble gelling agent and a DNase indicator system as described herein. A second part of each kit may be selected from the group of accessory articles consisting of a membrane filter, a pipette, a spreader, a glove, a sample acquisition device, a capture element, a sample-suspending medium, a reagent, and any combination of two or more of the foregoing accessory articles.

Membrane filters should be of a shape and size that is suitable for fitting into the aperture of the spacer of the culture plate device of the kit. Filters of different kinds can be provided with a kit, or multiple kits can contain various filters. The filters are optional and, preferably, provided in aseptic condition such as a polyethylene coated paper package which has been sterilized by gamma irradiation, ethylene oxide or other sterilization. Alternatively the filters may be nonsterile units which are to be sterilized by the user.

Suitable pipettes and spreaders can be made from, for example, plastic or glass. The pipettes and spreaders can be provided in a pre-sterilized condition or can be provided in a nonsterile condition. The pipettes and spreaders can be disposable after a single use or can be resterilized for multiple uses. "Pipettes", as used herein include volumetric pipettes with at least one gradation mark corresponding to a known volume and pipette tips, which can be used with a volumetric pipetting device. The kit can contain a package of reagents. The reagents are preferably contained in a sterile package for example a foil package such as those conventionally used in the pharmaceutical industry. An example of such a package is used for NITRO-BID Ointment (Marlon Laboratories, Inc., Kansas City, Mo.). The selection of the reagents useful and necessary in the kits may depend upon the microorganism to be evaluated.

The invention will be further illustrated by reference to the following non-limiting Examples. All parts and percentages are expressed as parts by weight unless otherwise indicated. Unless specified otherwise, all reagents were obtained from Sigma Chemical Company (St. Louis, Mo.).

EXAMPLES

Example 1

Detection of Growth and DNase Activity in PETRIFILM Aerobic Count Plates

Phosphate-buffered saline (PBS) was obtained as a 10× concentrate (OmniPur 6505; EMD Chemicals; Gibbstown, N.J.). DNA (sodium salt, from salmon testes) and methyl green dye (zinc chloride salt, Aldrich 198080-10G) were obtained from Sigma-Aldrich (St. Louis, Mo.). λ-carrageenan (viscarin GP 109F type) was obtained from FMC BioPolymer (Philadelphia, Pa.). 3M PETRIFILM Aerobic Count Plates and the PETRIFILM Plate Reader (PPR) were obtained from 3M Company (St. Paul, Minn.). *S. aureus* ATCC 25923 (DNase positive, methicillin-sensitive) was obtained from the American Type Culture Collection (Manassas, Va.). *S. epidermidis* strain 472 (DNase-negative) and *S. aureus* strain 565 (DNase positive, methicillin-resistant) were obtained from clinical isolates.

A solution of DNA-PBS solution was prepared by adding 2.0 mg/mL DNA and 0.1 mg/mL λ carrageenan to 1× (10 mM) PBS. The mixture was boiled in a covered container until DNA dissolved. Stock solutions of DNA-PBS-MG were prepared by adding 100 µg/mL and 50 µg/mL, respectively, methyl green dye to aliquots of the DNA-PBS solution. Portions of the DNA-PBS-MG stock solutions were diluted with various amounts of the DNA-PBS buffer to make solutions containing a predetermined concentration of PBS and DNA (2 mg/mL) with various concentrations (from 0-60 µg/mL) of methyl green dye. All of the solutions were autoclaved at 250° C. for 15 minutes.

Broth cultures of the bacteria were prepared by inoculating individual tubes containing 1 mL of tryptic soy broth medium and incubating tubes overnight at 37° C. The bacteria were pelleted by centrifugation, washed and resuspended in sterile PBS. The resuspended cells were diluted (1:10 serial dilutions) in sterile PBS. The two highest dilutions ($10^{-4}$ and $10^{-5}$, respectively) were diluted 1:100 into the appropriate solution of PBS-DNA-MG and 1 mL of each diluted mixture was used to inoculate a PETRIFILM Aerobic Count Plate according to the manufacturer's instructions. Control plates (without bacteria) were likewise inoculated. The plates were incubated at 35° C. for approximately 20 hours. Plates containing colonies that numbered in the countable range (i.e., between 25-250 colonies) were selected for evaluation. The growth results are shown in Table 2. The selected plates were imaged using a Petrifilm Plate Reader that was set up with the standard PETRIFILM Aerobic Count Plate settings.

The bitmap images generated by the PPR were imported into Adobe PhotoShop® software (Adobe Systems, San Jose, Calif.). The software was used to view the red channel of the image to visualize clearing zones around the colonies due to DNase activity associated with the colony. Bacterial colonies were detected by two different means: i) the colonies reduced the colorless tetrazolium indicator in the plate to a red formazan dye that was visible to the eye and was observable in images of the plates and ii) DNase-producing colonies interacted with the DNase indicator system to produce a colorless zone surrounding the colony. The zones were visible to the eye at all concentrations of methyl green that were tested. The zones were easily visible, at all concentrations of methyl green tested, in the red images produced by the Petrifilm Plate reader. The data indicated that higher concentrations of methyl green inhibited the growth of some microorganisms. Results are summarized in Table 2.

Example 2

Analysis of Petrifilm Plate Images

PETRIFILM Aerobic Count plates were prepared as described in Example 1. The plates were inoculated with *S. aureus* ATCC 25923, a DNase-producing microorganism. After inoculation, the hydrogel in the plates contained 20 µg/mL methyl green. A plate was imaged using a PETRIFILM Plate reader as described in Example 1.

Figure 7A:
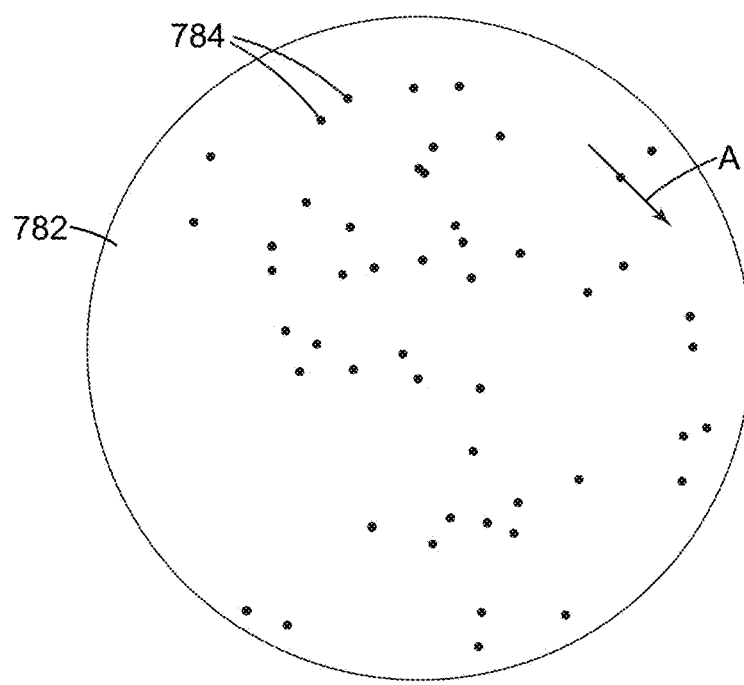
FIG. 7a is a representation of a black-and-white image of a PETRIFILM plate illuminated with green light-emitting diodes with a selected area of interest represented by line A.
Figure 8A:
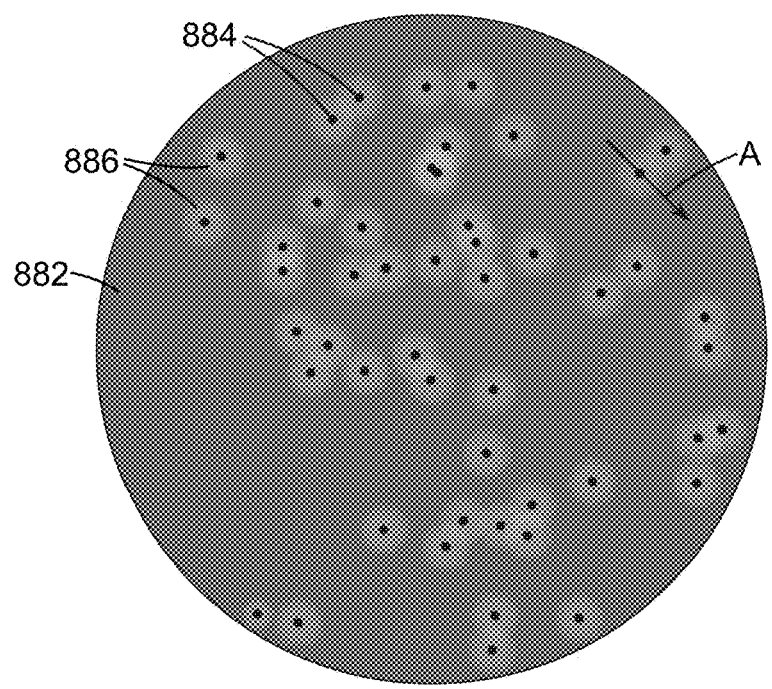
FIG. 8a is a representation of a black-and-white image of a PETRIFILM plate illuminated with red light-emitting diodes with a selected area of interest represented by line A.

The red, green and blue images were exported into IMAGE-PRO Plus version 6.3.0.512 software. Representations of the grayscale images of the plate when illuminated with green or red LED's are shown in FIGS. 7a and 8a, respectively. The plate grid lines, which were quite visible in the green-illuminated image but not visible in the red-illuminated image, have been omitted from the figures.

FIG. 7a shows the hydrogel 782 in the inoculated portion of the plate. Also shown are several bacterial colonies 784. A region of interest, running from pixel x,y coordinates of (813, 292) to (904, 380), was selected using the line profile tool of the Image Pro Plus software and is represented in the figure as line A. Pixel intensity data was extracted using the image analysis software and is plotted in FIG. 7b as a function of the distance along line A. The intensity value is proportional to the amount of light reflected by the hydrogel and objects therein.

Figure 7B:
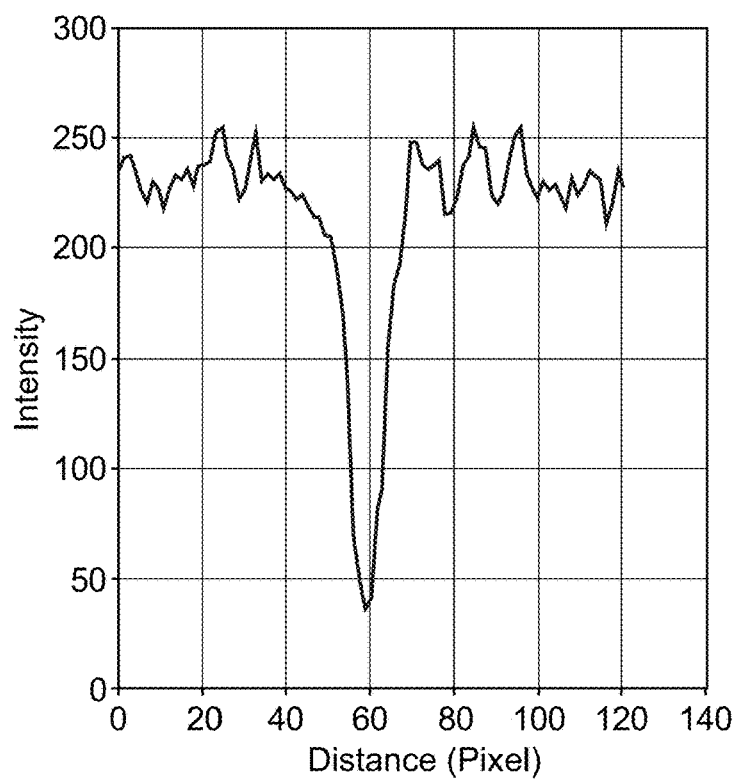

The data in FIG. 7b show that, except for the area occupied by the bacterial colony (i.e., from pixel distance of about 50 to pixel distance of about 65), there is very little absorption of green light by the hydrogel in the region of interest.

FIG. 8a shows the hydrogel 882 in the inoculated portion of the plate. Also shown are several bacterial colonies 884. The same region of interest (as FIG. 7a) was selected for this image and is represented as line A. Pixel intensity data was extracted using the image analysis software and is plotted in FIG. 8b as a function of the distance along line A.

Figure 8B:
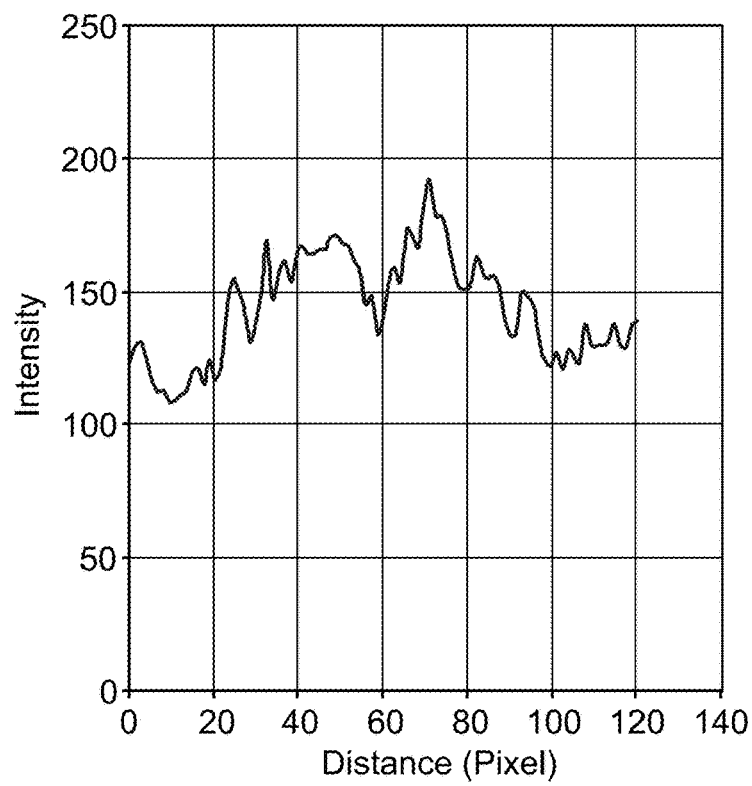

The data in FIG. 8b show that, in contrast to the data from the green image, the area occupied by the bacterial colony (i.e., from pixel distance of about 50 to pixel distance of about 65) shows very little absorption of red light. Also in contrast to the data from the green image, FIG. 8b shows that there is more absorption of red light by the hydrogel as you move away from the colony and that the amount of absorption of red light proximate the colony decreases relative to the rest of the hydrogel, showing that the zone of DNA hydrolysis surrounding the colony is detected by higher pixel intensities in the hydrogel surrounding the colony.

TABLE 2

Visual detection of colonies. The plates were observed and the results either observed by eye or by viewing the full-color image produced by the PPR are reported below.

| Methyl Green µg/mL | Strain 472 | Strain 25923 | Strain 565 |
|---|---|---|---|
| 0 | small, dark-red colonies. | medium-sized, red colonies. | medium-sized, red colonies. |
| 10 | small, dark-red colonies. No clear zones. | medium-sized, red colonies. Faint clear zones. | medium-sized, red colonies. Faint clear zones. |
| 20 | small, dark-red colonies. No clear zones. | medium-sized, red colonies. Distinct clear zones present. | medium-sized, red colonies. Distinct clear zones present. |
| 30 | small, dark-red colonies. No clear zones. | medium-sized, red colonies. Distinct clear zones present. | medium-sized, red colonies. Distinct clear zones present. |
| 40 | small, dark-red colonies. No clear zones. | medium-sized, red colonies at outer edge of plate. Smaller colonies at center of the plate. Distinct clear zones present. | medium-sized, red colonies at outer edge of plate. Smaller colonies at center of the plate. Distinct clear zones present. |
| 50 | small, dark-red colonies. No clear zones. | medium-sized, red colonies at outer edge of plate. Smaller colonies at center of the plate. Distinct clear zones present. | medium-sized, red colonies at outer edge of plate. Smaller colonies at center of the plate. Distinct clear zones present. |
| 60 | small, dark-red colonies. No clear zones. | Far fewer colonies than control plate. Most visible colonies were at outer edge of plate. Distinct clear zones present. | Far fewer colonies than control plate. Most visible colonies were at outer edge of plate. Distinct clear zones present. |

Example 3

Early Detection of DNase-Producing Microorganisms

Prepared PBS-DNA solutions with (50 µg/mL) and without methyl green, as described in Example 1. A final concentration of 20 µg/mL was used for methyl green in all of the plates that contained methyl green in this experiment A suspension of washed bacterial cells (*Staphylococcus aureus* ATCC strain 25923) was prepared as described in Example 1. The suspension was diluted and inoculated into Petrifilm Aerobic Count Plates as described in Example 1.

The inoculated plates were placed on top of a metal heat block set to 37° C. A NIKON E8400 digital camera (Nikon, Inc., Melvelle, N.Y.) was positioned above the plates. The camera was linked to a computer through IMAGE-PRO Plus version 6.3.0.512 software, which was programmed to take digital photos of the plates every 30 minutes for 24 hours. An insulated cover was placed over the camera and heat block apparatus to keep the temperature of the plates at 37° C. Preprogrammed settings for the digital camera are shown in Table 3. Table 3. Digital camera settings for photos taken in Example 3.

| CAMERA: | E8400V1.1 |
|---|---|
| METERING: | MATRIX |
| MODE: | P |
| SHUTTER: | 1/96 sec |
| APERTURE: | F5.0 |
| EXP +/−: | 0.0 |
| FOCAL LENGTH: | f15.2 mm(X1.0) |
| IMG ADJUST: | AUTO |
| SENSITIVITY: | AUTO |
| WHITEBAL: | INCANDESCENT |
| SHARPNESS: | AUTO |
| QUALITY: | 3264 × 2448 EXTRA |
| SATURATION: | 0 |
| FOCUS AREA: | CENTER |

Digital photos were imported into Adobe Photoshop version 5.5 and the red channel of each image was viewed. All images were magnified (150-200×) when viewed. In general, colonies appeared as gray spots on the red channel images of the plates and colonies appeared as red spots on the full-color images of the plates. *S. aureus* colonies were visible in the red channel images within 9.5 hours after inoculation. Thin, white zones of DNase activity were visible in the red channel images within 11.5 hours after inoculation. In contrast, colonies were not visible on the color images of the same plates until after 10 hours of incubation and clearing zones were not visible on the color images of the same plate until after 12 hours of incubation. Table 4 shows a summary of the results observed for each plate from 9-15 hours of incubation.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A detection article, comprising:
   a body member comprising a self-supporting, waterproof substrate having upper and lower surfaces;
   wherein a dry coating comprising a cold water-soluble gelling agent and an indicator system is adhered uniformly onto a portion of at least one surface of the body member;
   wherein the indicator system comprises DNA and methyl green; and
   wherein, after contact with a predetermined volume of an aqueous liquid, the gelling agent forms a hydrogel and the concentration of methyl green in the hydrogel is about 5 µg/mL to about 20 µg/mL.

2. The article of claim 1, wherein the coating further comprises a nutrient medium, an indicator, a selective agent, or any combination of two or more of the foregoing.

3. The article of claim 2, wherein the selective agent selects for the growth of *Staphylococcus aureus*.

4. The article of claim 3, wherein the selective agent is selected from the group consisting of cephalothin, cefazolin, cephradine, cephalexin, cefadroxil, cefamandole, cefoxitin, cefaclor, cefuroxime, cefuroxime axetil, loracarbef, cefonicid cefotetan, ceforanide, cefotaxime, cefpodoxime proxetil, ceftizoxime, cefixmeceftriaxone, cefoperazone, ceftazidime, moxlactam, cefepime, cefpirome, and oxacillin.

* * * * *

TABLE 4

Visual interpretation of the images of two plates taken from 9-15 hours after inoculation. The plates contained 0 µg/mL and 20 µg/mL methyl green, respectively.

| | Color images | | Red channel images | |
|---|---|---|---|---|
| hrs | 0 µg/mL MG | 20 µg/mL MG | 0 µg/mL MG | 20 µg/mL MG |
| 9.0 | No colonies | No colonies or clearing | No colonies | No colonies or clearing |
| 9.5 | No colonies | No colonies or clearing | No colonies | Two very small colonies |
| 10.0 | About 5 very small colonies | One very small colony; no zone | No colonies | Two very small colonies; no zones |
| 11.0 | About 80 very small colonies | About 3 very small, colonies, no zones | Very small colonies | About 3 very small colonies; no zones |
| 11.5 | About 110 very small colonies | About 3 very small, colonies, no zones | Numerous very small colonies | About 3 very small colonies with very thin white rings |
| 12.5 | About 110 very small colonies | About 15 very small colonies, small zones around largest ones | About 80 very small colonies | About 4 very small colonies with thin white rings; some colonies without rings |
| 15.0 | About 110 very small colonies | About 50 colonies, small clear zones surrounding about 25 | About 101 small colonies | About 45 very small colonies with small distinct clear zones |

UNITED STATES PATENT AND TRADEMARK OFFICE
CERTIFICATE OF CORRECTION

PATENT NO. : 10,280,446 B2
APPLICATION NO. : 15/651164
DATED : May 7, 2019
INVENTOR(S) : Patrick Mach et al.

It is certified that error appears in the above-identified patent and that said Letters Patent is hereby corrected as shown below:

In the Specification

Column 1
Line 44, delete "0" and insert -- O --, therefor.

Column 2
Line 38, delete "cefixmeceftriaxone," and insert -- cefiximeceftriaxone, --, therefor.
Line 38-39, delete "moxlactam, cefipime," and insert -- moxalactam, cefepime, --, therefor.

Column 3
Line 19-20, delete "cefixmeceftriaxone," and insert -- cefiximeceftriaxone, --, therefor.
Line 20, delete "moxlactam, cefipime," and insert -- moxalactam, cefepime, --, therefor.
Line 60-61, delete "cefixmeceftriaxone," and insert -- cefiximeceftriaxone, --, therefor.
Line 61, delete "moxlactam, cefipime," and insert -- moxalactam, cefepime, --, therefor.

Column 12
Line 27, after "species)" insert -- . --.

Column 13
Line 10 (approx.), delete "mglcm2" and insert -- mg/cm2 --, therefor.
Line 10 (approx.), delete "mglcm2." and insert -- mg/cm2. --, therefor.

Column 20
Line 14, after "695" insert -- . --.

Column 22
Line 11, delete "cefixmeceftriaxone," and insert -- cefiximeceftriaxone, --, therefor.
Line 12, delete "moxlactam," and insert -- moxalactam, --, therefor.
Line 52, delete "choride)," and insert -- chloride), --, therefor.
Line 55, delete "bromthymol" and insert -- bromothymol --, therefor.

Signed and Sealed this
Nineteenth Day of November, 2019

Andrei Iancu
*Director of the United States Patent and Trademark Office*

Column 23
Line 4, delete "Melvelle," and insert -- Melville, --, therefor.
Line 21, delete "and or" and insert -- and/or --, therefor.
Line 25, delete "and or" and insert -- and/or --, therefor.

Column 26
Line 65, after "experiment" insert -- . --.

Column 27
Line 5, delete "Melvelle," and insert -- Melville, --, therefor.

In the Claims

Column 28
Line 40, in Claim 4, delete "cefixmeceftriaxone," and insert -- cefximeceftriaxone, --, therefor.
Line 41, in Claim 4, delete "moxlactam," and insert -- moxalactam, --, therefor.